United States Patent
Rainey

(10) Patent No.: US 6,253,964 B1
(45) Date of Patent: Jul. 3, 2001

(54) REMOTELY ACTUABLE FLUSHING SYSTEM

(76) Inventor: J Tim Rainey, 403 Commerce, Refugio, TX (US) 78377

(*) Notice: Subject to any disclaimer, the term of this patent is extended or adjusted under 35 U.S.C. 154(b) by 0 days.

(21) Appl. No.: 09/613,402

(22) Filed: Jul. 11, 2000

Related U.S. Application Data

(63) Continuation of application No. 09/187,155, filed on Nov. 6, 1998, now abandoned.
(60) Provisional application No. 60/066,984, filed on Nov. 28, 1997, provisional application No. 60/073,739, filed on Feb. 5, 1998, and provisional application No. 60/079,342, filed on Mar. 25, 1998.

(51) Int. Cl.[7] .................................................. B67D 1/08
(52) U.S. Cl. ............................................................ 222/148
(58) Field of Search ............................................. 222/148

(56) References Cited

U.S. PATENT DOCUMENTS

| | | | |
|---|---|---|---|
| 4,051,034 | * | 9/1977 | Amon et al. ......................... 222/148 |
| 4,691,850 | * | 9/1987 | Kirschmann et al. ................ 222/148 |
| 5,528,841 | * | 6/1996 | Detsh et al. ......................... 222/148 |

* cited by examiner

Primary Examiner—Philippe Derakshani
(74) Attorney, Agent, or Firm—Kilpatrick Stockton LLP

(57) ABSTRACT

A self cleaning fluid distribution system for clean water applications including a water source interconnected to a sterilizing or disinfecting fluid source by a fluid conveyance system. The fluid conveyance system configurable for dispensing both water and disinfectant fluid from said system and for automatedly circulating disinfecting fluid through a substantial entirety of said system in a self-sterilizing/disinfecting process.

6 Claims, 1 Drawing Sheet

REMOTELY ACTUABLE FLUSHING SYSTEM

RELATED PATENT APPLICATIONS

This is a continuation of application Ser. No. 09/187,155, filed Nov. 6, 1998 now abandoned which claims benefit to U.S. Provisional Application No. 60/066,984 filed Nov. 28, 1997, No. 60/073,739 filed Feb. 5, 1998 and No. 60/079,342 filed Mar. 25, 1998. Said applications in their entirety are hereby expressly incorporated by reference into the present application.

DESCRIPTION

1. Technical Field

The present invention relates generally to systems used in dental procedures; and more specifically, systems used to supply and dispense clean water and air during dental procedures.

2. Background Art

There are many procedures performed in dental offices that require clean water and clean air. Either of these fluids may be dispensed into a patient's mouth for various reasons. Water may be used as a flushing medium and air may be used as a dryer. In either event, it is important that the fluid introduced be as free as possible of contaminants. Because many of the dental procedures within which these fluids will be dispensed deal with open patient wounds, contaminated fluids are likely to cause infection. It is well known to use a clean solution source such as bottled, sterile or distilled water or saline solution.

Contamination may be introduced into the fluid delivery system from two primary sources. The first is from the air supply that is used to pressure the bottled water. The sterile or distilled water may begin bacteria and virus free, but if contaminated air is pumped into the bottle for pressuring the water, that water will also become contaminated. Secondly, bacteria can be introduced into the delivery system from the instruments placed within a patient's mouth. A phenomenon commonly referred to as a suck-back action often occurs when a fluid being dispensed is abruptly shut off. When this occurs, a small amount of fluid may be hydraulically pulled back into the delivery system where it can be harbored and multiplies. Once this bacterial and viral contamination enters the dispensing system, it can multiply, grow and migrate further back into the system. This migration may theoretically continue, unless stopped, all the way back to the source bottle thereby contaminating the entire sterile water or saline solution supply. As a result of these two sources of contamination, there is an increased possibility for a patient exposure to such contaminants. Clearly, it is a goal of dental care providers to eliminate such contamination and assure that the air and water dispensed to a patient is clean in the sense that it is as free as possible from particulate, bacteria and viruses.

In view of the above described deficiencies associated with the use and designs of known air and water delivery systems for dental procedures, the present invention has been developed to alleviate these drawbacks and provide further benefits to the user. These enhancements and benefits are described in greater detail hereinbelow with respect to several alternative embodiments of the present invention.

DISCLOSURE OF THE INVENTION

The present invention in its several disclosed embodiments alleviates the drawbacks described above with respect to known air and water delivery systems for dental procedures. More specifically, the two sources for contamination introduction into the delivery system have been minimized. Regarding contamination that is airborne from a pressured air supply, an in-line, point of use filter is incorporated that removes harmful particulate, bacteria and virus. A 0.1 micron coalescing filter is placed in-line after the air supply, but before the air manifold of the fluid delivery system. In addition to the filter, a regulator and check valve are also provided for enhancing the performance of the delivery system. The regulator is used to assure that a constant and uniform air pressure is supplied to the delivery system and the check valve is incorporated to prevent back flows into the filter and air supply system. Because of the check valve, when pressure is relieved from the air supply side, already introduced gas and possibly even liquids are prevented from backing up and potentially contaminating the filter and air source. In this manner, future provision of clean air is further assured.

Contamination resulting from the suck-back action is dealt with using a disinfecting/sterilizing wash through the delivery system and dental instruments used upon a patient. The disinfectant/sterilant is not only used to clean the delivery system, but it may also be dispensed into the patient's mouth to produce a foaming and sometimes therapeutic action.

One drawback of the application of the disinfectant into a patient's mouth is its extreme offensive taste to some persons. As a result, many dental professionals and practitioners are reluctant to use such disinfectants in a patient's mouth, in spite of the possible therapeutic benefits for fear that the taste will offend the patient. The present invention relieves such apprehension by providing a ready means for quickly and selectively changing the flow to the patient from the possibly distasteful disinfectant back to clean water immediately upon detecting a negative reaction from the patient.

The delivery system is also configured so that a circulation of disinfecting fluid can be established through the portions of the delivery system that may potentially become contaminated from suck-back action or other source of contamination. This is accomplished by purging water within the system with disinfectant solution from as far back upstream as the top of the distilled or treated water bottle and up to and through the various dental instrument tips. To further ensure decontamination of the system, the present invention contemplates a daily flushing procedure wherein a disinfecting/sterilizing purge is affected at the end of a working day and held within the delivery system until purged on the following morning with distilled or otherwise treated water prior to a first patient application.

In dental offices where only typical dental procedures are being performed, the disinfecting purge is required once a day as indicated above. When surgeries are being performed and the risk of infection is heightened, the disinfecting/ sterilizing purge procedure should be effected between each operation. If the flushing process is manually controlled, it would not be uncommon for an attendant to be required to spend a significant amount of time in each treatment room both in the evening and in the following morning performing the purging process. As a result, automation of the disinfecting purge process is highly advantageous and can be easily accomplished through the use of automated valve assemblies. In circumstances where between-patient flushing is desired, the frequency of the purging processes will not be uniform across the several operatories or treatment rooms and must therefore be initiatable by an operator. In the instance of purging systems having automated valve controls, however, the operator need only initiate the purging process but is not required to remain in attendance through its completion.

So as to further eliminate the need for operator initiation of these regularly scheduled disinfecting/sanitizing procedures, it is contemplated that each purging system of the several treatment rooms of a particular office be automated and centrally and remotely controlled. By adding the enhancement of controlling such operations on a timed basis, the need of an attendant for daily purging procedures is entirely eliminated. Such coordination and automation may be easily accomplished through known remote communication systems that may be utilized for controlling such purging processes.

With these principles in mind, the methods and apparatus disclosed herein as being associated with clean water should be taken as generically applicable in settings such as traditional dental offices, the medical fields, veterinary practices, industrial processes and other applications and environments requiring clean water. In this same vane, clean water is considered to be that which has been filtered of particulate, disinfected, sterilized and/or otherwise rid of contamination.

The general beneficial effects described above apply generally to each of the exemplary descriptions and characterizations of the devices, mechanisms and systems disclosed herein. The specific structures through which these benefits are delivered will be described in detail hereinbelow.

BRIEF DESCRIPTION OF THE DRAWINGS

The invention will now be described in greater detail in the following way of example only and with reference to the attached drawings, in which.

MODE(S) FOR CARRYING OUT THE INVENTION

Figure 1:
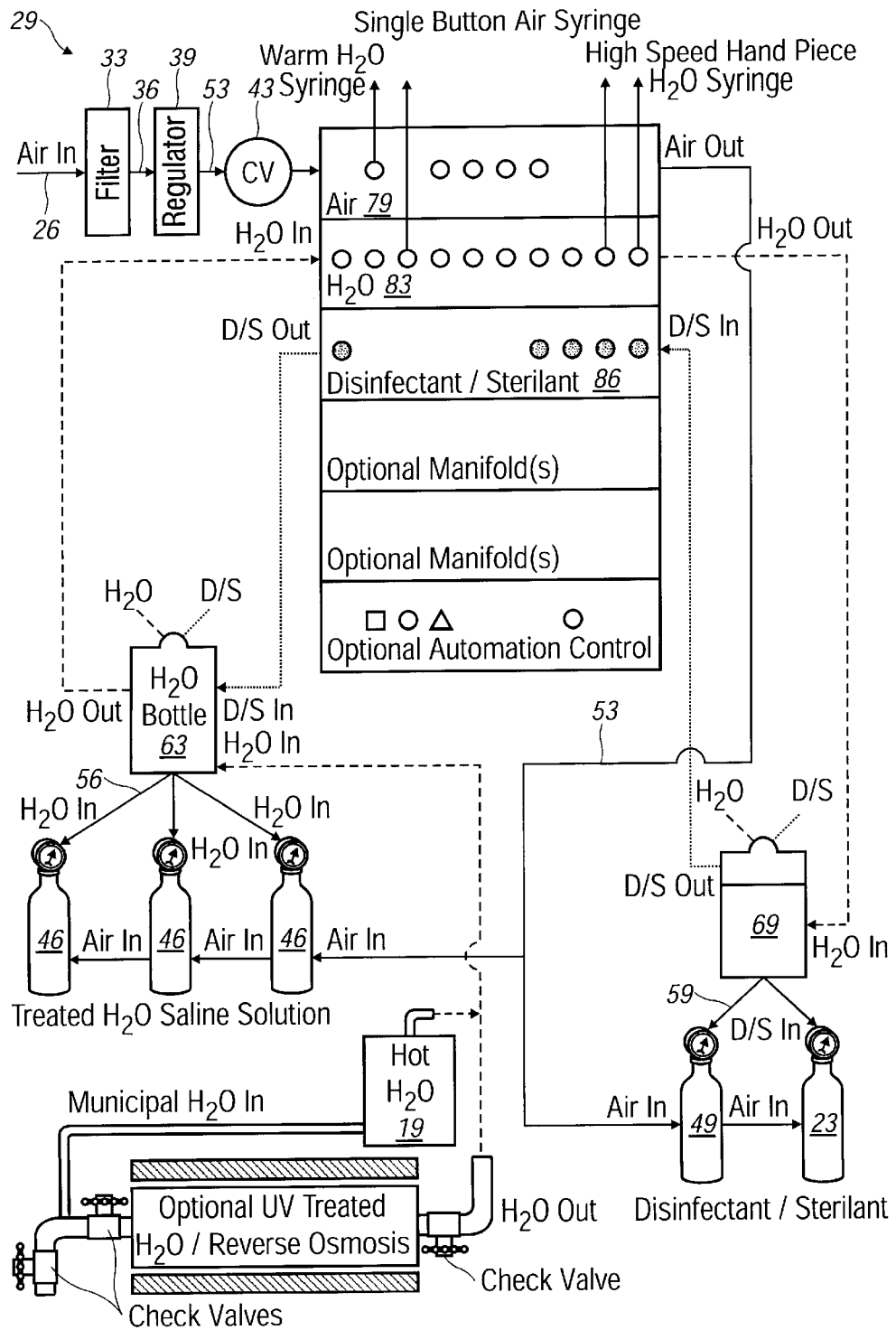
FIG. 1 is a schematic drawing illustrating the several components of the self-cleaning fluid dispensing system disclosed herein and the corresponding method(s) of utilization.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a basis for the claims and as a representative basis for teaching one skilled in the art to variously employ the present invention.

Referring to FIG. 1, the several components that make up the present invention of a clean fluid dispensing dental system are illustrated. Generally, a fluid delivery system 69 is shown comprising an air manifold 79, a water manifold 83 and a disinfectant manifold 86. Each manifold is pressurable with the indicated fluid for dispensation through various outlets. The air manifold 79 receives pressured gas from a compressed gas or air source 26. It should be appreciated that the gas being utilized in the present system may not necessarily be air, but may be other appropriate gases utilized in medical and dental settings. In the drawing, conduits conducting treated water are cross-hatched, conduits conducting air are straight-line, and conduits conducting cleaning fluid are beaded for clarity.

As explained above, it is important that the air dispensed to a patient and used to pressure various supply fluids of the system be substantially clean from particulate, bacteria and viruses. The cleansing of the source air is accomplished through the utilization of a point-of-use filter 29 having a characteristic porosity of not more than 0.1 milli-micron. In the preferred embodiment, the filter 29 is of the coalescing type and is capable of removing offending particulate, as well as contaminating bacteria and viruses. The filter 29 is positioned interstitially in the air supply line and is housed within a transparent filter bowl 33 commonly constructed from polycarbonate. Because the bowl 33 is transparent, the condition of the filter 29 may be visually observed and replacement affected when necessary. A closable drain 36 is provided at the base of the filter bowl 33 so that collected fluids from filtration may be drained therefrom. A regulator 39 is provided upstream or downstream from the filter 29 and is used to assure a uniform pressure supply to the various components of the fluid dispensing system. A check valve 43 is placed in-line downstream from the regulator, but before introduction into the air manifold for assuring one-way fluid movement. The check valve prevents back-wash of fluid into the air supply system behind that check valve 43 when pressure is removed at the source 26.

Once the air or other gas has been supplied to the air manifold 79, it is dispensable to the various instruments requiring pressured gas and to the supply bottles of clean water and disinfectant/sterilant. Since the air supplied thereto is clean, those bottled sources are assured to remain clean, provided they are originally clean.

As described above, the fluid delivery system 69 includes a plurality of manifolds including in the illustrated embodiment an air manifold 79, a water manifold 83 and a disinfectant/sterilant manifold 86. Each manifold is selectively pressurable with the indicated fluid. From each manifold, various outlets are provided for dispensing fluid to various end uses. As an example, fluid dispensing syringes may be tapped into outlets on either of the different manifolds. The typical syringes are well known to dental professionals and practitioners, and most patients who frequently visit these health care, providers. When tapped into either of the manifolds, such a syringe may be button actuated to dispense the required fluid upon demand. The use of different fluids may be selected by transferring the inlet tap of the particular instrument. As an example, a button actuated, hand-held dental instrument 06 may be an air delivery instrument 09 tapped into the air manifold 79, a water delivery instrument 11 tapped into the water manifold 83, a disinfectant delivery instrument 13 tapped into the disinfectant/sterilant manifold 86 or even a hot water delivery instrument 16 if tapped into the hot water heater 19 fluid supply. Any of these delivery instruments may be referred to as fluid dispensers. In specific configurations of the clean water system, any of these delivery instruments may be permanently tapped to the appropriate manifold or fluid source, or they may be releasably connectable using quick disconnects that facilitate their exchange.

A pressured sterile solution bottle 46 is included that may contain treated water, distilled water or saline solution, among others. A pressured disinfectant solution bottle 49 is also provided. Each of these bottled sources of solution are pressured by clean air distributed from the air manifold 79. Because the pressuring force comes from this common manifold source, like pressure is applied to each bottle and therefore each fluid is dispensable at similar pressure. Alternatively, the pressuring force on each bottle may come from different sources and different driving pressures may be applied to the different bottles thereby making the different fluids dispensable at different pressures.

The introduction of both water and disinfectant into the delivery system 69 is controlled by two user operable control valves 63 and 66. The water/flush control valve 63 determines whether or not clean water or disinfectant is supplied to the water manifold 83. The disinfectant control valve 66 governs whether or not disinfectant or clean water is supplied to the disinfectant manifold 86. Both the water manifold 83 and the disinfectant manifold 86 have dispensing outlets to the other control valve opposite to that valve which controls the input of fluid into the particular manifold. Through this configuration, it is possible to establish a complete disinfectant flush through the delivery system 69, as well as toggle between the dispensation of disinfectant and clean water from the disinfectant manifold 86.

As described above, dental professionals and practitioners may be hesitant to administer disinfectant to a patient in spite of potential beneficial effects because of some patient's negative reaction to a sensed bad taste. To alleviate the user's hesitancy, the disinfectant control valve 66 makes it possible to administer disinfectant through an instrument tapped into the disinfectant manifold 86, but quickly switch over to clean water if a negative reaction is detected. This is accomplished by configuring the disinfectant control valve 66 from a position wherein fluid is supplied from the pressured disinfectant solution bottle 49 to a supply outlet from the pressured water manifold 83. By affecting such a switch, the user can quickly stop the flow of disinfectant and flush the offending disinfectant from the patient's mouth using clean water. It should be appreciated that the configuration of the manifold of FIG. 1 is shown for illustration purposes and may be variously designed according to specifications of the incorporating system.

Regarding the possible contamination experienced because of the suck-back phenomenon or contamination other sources, appropriate connections are established through water conduits 56 and disinfectant/sterilant conduits 59 that permit the circulation of disinfectant throughout the portions of the delivery system 69 that have the potential for suck-back contamination. Specifically, the water/flush control valve 63 may be toggled to a flush configuration wherein pressured disinfectant/sterilant 23 is drawn through that control valve 63 in line to the pressured solution bottle 46, supplied to the water manifold 83 and dispensed out of water delivery instruments 11 tapped into that manifold 83. In so doing, a disinfecting circuit is established that purges possibly contaminated fluids from the delivery system 69. The disinfectant/sterilant may be held within the system 69 for an extended period, such as overnight, to assure that recontamination does not occur before a subsequent flushing with clean water. Furthermore, whether or not the cleaning solution acts as a disinfectant or a sterilant is primarily dependent upon the period to time the cleaning solution is retained within the line or vessel to be cleaned. For disinfecting purposes, the cleaning solution must be present in the line or vessel for several minutes. For sterilizing purposes, the cleaning solution must be present in the line or vessel for an extended period, such as overnight. In general terms, both situations have been referred to herein as being for cleaning purposes.

As may be appreciated in FIG. 1, the hot water heater 19 and delivery instruments 16 off of that heater may also be disinfected/sterilized if those instruments 16 are actuated causing disinfectant to be drawn therethrough during a flush cycle.

As indicated above, the purging process in which disinfectant is circulated and ultimately flushed through the delivery systems can be manually actuated and controlled. Such requirements, however, can be easily eliminated by automating the control of the several valves and then controlling those automated valves centrally and remotely. Such control may be effected using known automation control systems that communicate actuating and other processing control commands to each treatment room's individual systems and components. In this manner, the flushing procedures can be made to be automatic and caused to occur regularly with respect to time or other controlling events. At a minimum, these flushing procedures will occur on a daily basis, typically overnight when the disinfectant may be permitted to remain within the system effecting a more thorough sanitation. As a result, the more frequent flushings throughout the day may be operator initiated, but because the flushing process has been automated, it will not be required that that operator remain in attendance for controlling any portion of the procedure after initiation. In this manner, personnel costs may be reduced and the consistency and uniformity of the disinfecting procedures can be better assured.

As is well known in the automation arts, control from a central processor may be communicated to the individual systems and components using hard wire electrical transmissions; alternatively, radio or other wave-based communication may be utilized depending upon the requirements of each particular environment of use. In each case, those skilled in the art of automating such processes will readily appreciate the various and different techniques that may be utilized in effecting the automation described herein.

The above described dispensing system may not have adequate water supply using the pressured sterile solution bottle 46 alone. Some dental procedures such as the use of micro-abrasive techniques require a significantly greater amount of water for irrigation purposes than most other conventional dental procedures. As a result, daily uses of several ounces of water may exponentially increase to as much as a gallon of water per hour. Consequently, the use of bottled water is impractical and an alternative for supplying greater quantities of clean water is desirable.

Therefore, an optional feature has been contemplated which includes sufficiently heating or otherwise treating the water supplied from a municipal tap to pasteurize or treat the water and kill or remove harmful pathogens contained therein. The water is then drained from the heating tank into a reservoir that serves as a supply tank to the dispensing system described above Logistically, the connection of this op al clean water supply would be upstream of the water manifold 83.

An ability to toggle between the water supplied from a pressured bottle 46 to the optional treated water supply would be required. A municipal water tap may serve as an input into a pasteurizing water heater or other suitable type of water treating system. Alternative suitable cleansing methods may include treating source water utilizing UV light, reverse osmosis and mechanical filtration.

In one of the illustrated embodiments, a heating coil or other means for supplying sufficient heat to kill included pathogens is conductively associated with the heater tank. A check valve provided upstream from the municipal supply prevents backflow into the municipal supply. A temperature sensor may be exposed within the heater tank which detects and relays information to circuitry that engages the heating element cyclically to assure that each filling of the heater tank is sufficiently raised. After that temperature is reached and sufficient pasteurization has occurred, the heat may be removed and the water permitted to begin cooling so that it is ready for patient application. Another option is to "clean" incoming tap water using ultra violet light. In either case, the goal remains to provide a more continuous and easily replenished supply of clean water to the system.

In the instance of heat pasteurization, water may be permitted to drain under gravitational influence either to a supply tank or alternatively to a drain for disposal. Flow to the supply tank may be governed by a solenoid operated valve between the heater tank and the supply tank that is controlled by two level sensors or switches that detect high and low-levels within the supply tank. In practice, when a low level is detected in the supply tank, the control valve is opened permitting inflow from the heater tank. Once the high level sensor is actuated, the valve is closed and backflow from the supply tank to the heater tank is prevented. With that pressure source removed, the pressured air source 26 must be placed in communication therewith providing pressure to the supply tank that expresses pasteurized water therefrom for being dispensed through the encompassing system 69.

Exemplarily, the supply tank includes a drain which permits the evacuation of all water held within the tank. The supply tank may also include a removable lid, that when closed, is air-tight so that the vessel may be pressurized, but the lid may also be removed to permit thorough disinfection and cleaning. The level sensors may be probes that extend into the supply tank and which are in electrical communication with the solenoid valve between the heater tank and the supply tank. Pressured air from the source 26 may be communicated to the supply tank and controlled by a three-way solenoid operated valve. In this manner, an exhaust configuration is permitted so that during filling of the supply tank, air may be released therefrom making room for the incoming pasteurized water. A tube may be provided for conveying pasteurized water that is to be dispensed from the reservoir tank and injected into the incorporating dispensing system 69. Preferably, the volume of water reservoired between the high and low levels of the supply tank is approximately one gallon. In this regard, the pasteurization process may be best described as a batch procedure wherein approximately one gallon of water is pasteurized in the water or head tank and a like amount is prepared for distribution in the supply or reservoir tank.

At the present time, those practitioners likely to appreciate the facilitation of this constant warm water source are those dentists utilizing micro-abrasive techniques that require significant irrigation water capabilities. The utilization of this option, however, is not limited to dental applications, but may also be incorporated into other industrial and medical settings where clean water is required in such large quantities that bottled water is not a suitable source. Based on the general design of the disclosed constant clean water supply source system, capacities for widely varying amounts of required water may be accommodated. It should be noted that if a continuous clean water supply source is chosen, the system's water storage bottle may be pressurized by the incoming water and a simple air space maintained in the bottle will help provide acceptable dispensation.

Although the present inventions have been described and illustrated in detail, it is to be clearly understood that the same is by way of illustration and example only, and is not to be taken as a limitation. The spirit and scope of the present invention are to be limited only by the terms of any claims that may be presented hereafter.

What is claimed and desired to be secured by Letters Patent is as follows:

1. A self cleaning distribution system for clean water applications comprising:
    a water source interconnected to a cleaning fluid source by a fluid conveyance system, said fluid conveyance system having a substantially constant gas pressure source interconnected to said water source and said cleaning fluid source by a gas conveyance system;
    a water control valve positioned in said fluid conveyance system between said water source and a fluid dispenser; and
    a cleaning fluid control valve positioned in said fluid conveyance system between said cleaning fluid source and said fluid dispenser for dispensing both water and cleaning fluid from said system and for circulating cleaning fluid through said system in a self-cleaning process.

2. A self cleaning fluid distribution system for dental applications comprising:
    a water source interconnected to a disinfecting fluid source by a fluid conveyance system, said fluid conveyance system configurable for dispensing both water and disinfecting fluid from said system and for circulating disinfecting fluid through said system in a self-cleaning process;
    a substantially constant gas pressure source interconnected to said water source and said disinfecting fluid source by a gas conveyance system for pressuring each of said water source and said disinfecting fluid source; and
    a water control valve positioned in said fluid conveyance system between said water source and a fluid dispenser for controlling dispensation of water from said water source.

3. A self cleaning fluid distribution system for dental applications comprising:
    a water source interconnected to a disinfecting fluid source by a fluid conveyance system, said fluid conveyance system configurable for dispensing both water and disinfecting fluid from said system and for circulating disinfecting fluid through said system in a self-cleaning process;
    a substantially constant gas pressure source interconnected to said water source and said disinfecting fluid source by a gas conveyance system for pressuring each of said water source and said disinfecting fluid source; and
    a disinfectant fluid control valve positioned in said fluid conveyance system between said disinfectant fluid source and a fluid dispenser for dispensing both water and disinfectant fluid from said system and for circulating disinfecting fluid through said system in a self-cleaning process.

4. A self cleaning fluid distribution system for dental applications comprising:
    a water source interconnected to a disinfecting fluid source by a fluid conveyance system, said fluid conveyance system configurable for dispensing both water and disinfecting fluid from said system and for circulating disinfecting fluid through said system in a self-cleaning process;
    a substantially constant gas pressure source interconnected to said water source and said disinfecting fluid source by a gas conveyance system for uniformly pressuring each of said water source and said disinfecting fluid source; and a disinfectant fluid control valve positioned in said fluid conveyance system between said disinfectant fluid source and a fluid dispenser, said disinfectant fluid control valve configurable for alternatively dispensing clean water and disinfectant fluid from said system.

5. A self cleaning fluid distribution system for a clean water dispenser comprising:

a clean water source interconnected to a disinfecting fluid source by a fluid conveyance system, said fluid conveyance system configurable for dispensing clean water and disinfecting fluid from said system and for circulating disinfecting fluid through said system in a self-cleaning process;

a gas pressure source interconnected to said clean water source and said disinfecting fluid source by a gas conveyance system for pressuring said clean water source and said disinfecting fluid source; and a fluid control valve positioned in said fluid conveyance system downstream of said clean water source and said disinfecting fluid source and upstream of a fluid dispenser for controlling dispensation of fluid from said system.

6. A self sterilizing distribution system for medical applications comprising:

a water source interconnected to a sterilizing fluid source by a fluid conveyance system, said fluid conveyance system configured with at least one substantially constant and uniform gas pressure source interconnected to said water source and said sterilizing fluid source by a gas conveyance system;

at least one water control valve in said fluid conveyance system positioned between said water source and said medical application; and at least one sterilizing fluid control valve in said fluid conveyance system positioned between said sterilizing fluid source and said medical application for dispensing both water and sterilizing fluid from said system and for circulating sterilizing fluid through a substantial entirety of said system in a self-sterilizing process.

* * * * *